(12) United States Patent
Niiranen et al.

(10) Patent No.: US 6,692,498 B1
(45) Date of Patent: Feb. 17, 2004

(54) BIOABSORBABLE, OSTEOPROMOTING FIXATION PLATE

(75) Inventors: Henna Niiranen, Tampere (FI); Pertii O. Tormala, Tampere (FI); Minna Kellomäki, Tampere (FI); Gerry Carlozzi, West Chester, PA (US)

(73) Assignee: Linvatec Corporation, Tampere (FI)

( * ) Notice: Subject to any disclaimer, the term of this patent is extended or adjusted under 35 U.S.C. 154(b) by 39 days.

(21) Appl. No.: 09/721,978

(22) Filed: Nov. 27, 2000

(51) Int. Cl.$^7$ ............................................... A61B 17/80
(52) U.S. Cl. ......................................................... 606/69
(58) Field of Search .................. 606/69, 70; 623/11.11, 623/16.11

(56) References Cited

U.S. PATENT DOCUMENTS

| | | | | | |
|---|---|---|---|---|---|
| 3,739,773 | A | * | 6/1973 | Schmitt et al. | 606/62 |
| 4,074,713 | A | * | 2/1978 | Capozza | 606/77 |
| 4,234,972 | A | * | 11/1980 | Hench et al. | 3/1.9 |
| 4,512,038 | A | * | 4/1985 | Alexander et al. | 3/1.9 |
| 4,715,860 | A | * | 12/1987 | Amstutz et al. | 623/22.33 |
| 5,108,399 | A | | 4/1992 | Eitenmuller et al. | |
| 5,380,328 | A | * | 1/1995 | Morgan | 606/70 |
| 5,413,577 | A | * | 5/1995 | Pollock | 606/69 |
| 5,466,262 | A | | 11/1995 | Saffran | |
| 5,807,396 | A | * | 9/1998 | Raveh | 606/69 |
| 5,904,720 | A | * | 5/1999 | Farrar et al. | 623/22.15 |
| 5,972,368 | A | * | 10/1999 | McKay | 424/422 |
| 6,093,201 | A | * | 7/2000 | Cooper et al. | 606/232 |
| 6,123,731 | A | * | 9/2000 | Boyce et al. | 623/23.63 |
| 6,206,883 | B1 | * | 3/2001 | Tunc | 606/77 |
| 6,221,075 | B1 | * | 4/2001 | Tormala et al. | 606/77 |
| 6,294,041 | B1 | * | 9/2001 | Boyce et al. | 156/275.5 |
| 6,294,187 | B1 | * | 9/2001 | Boyce et al. | 424/422 |

FOREIGN PATENT DOCUMENTS

| WO | 96 21628 A | 7/1996 |
|---|---|---|
| WO | 97 23171 A | 7/1997 |
| WO | 98 34553 A | 8/1998 |
| WO | 99 19005 A | 4/1999 |
| WO | 99 44529 A | 9/1999 |
| WO | 99 51171 A | 10/1999 |

OTHER PUBLICATIONS

International Search Report relating to PCT/IB00/01882.

* cited by examiner

Primary Examiner—Kevin Shaver
Assistant Examiner—Michael B. Priddy
(74) Attorney, Agent, or Firm—Kenyon & Kenyon

(57) ABSTRACT

The present invention relates generally to body tissue fixation systems, including body tissue fixation hardware comprising biocompatible, bioabsorbable plates, with an osteropromoting coating layer on at least one surface of said plates, and methods of using those system and hardware.

20 Claims, 11 Drawing Sheets

BIOABSORBABLE, OSTEOPROMOTING FIXATION PLATE

FIELD OF THE INVENTION

The present invention relates generally to body tissue fixation systems, including body tissue fixation hardware comprising biocompatible, bioabsorbable (resorbable), osteoconductive or osteoinductive plates, and methods of using those systems and hardware.

BACKGROUND OF THE INVENTION

Traditional orthopedic and traumatological fixation systems to facilitate bone fracture healing (osteosynthesis) typically employ metallic hardware, e.g., plates, screws, rods and the like, formed of biocompatible, corrosion resistant metals such as titanium and stainless steel. Typical metallic plates are described e.g. in the book F. Séquin and R. Texhammar, AO/ASIF Instrumentation, Springer-Verlag, Berlin, Heidelberg, 1981, at p. 21–22, 55–79, 107–108, 117–122, the entire disclosure of which is incorporated herein by reference. While such systems are generally effective for their intended purposes, they possess a number of inherent shortcomings. For example, metal release to the surrounding tissues has been reported. See, e.g., L.-E. Moberg et al. Int. J. Oral. Maxillofac. Surg. 18 (1989) at pp. 311–314. Other reported shortcomigs include stress shielding, see P. Paavolainen et al., Clin Orthop. Rel. Res. 136 (1978) 287–293), and growth restriction in young individuals, see K. Lin et al., Plast. Reconstr. Surg. 87 (1991) 229–235. In infants and young children there is the risk that metallic plates and screws can sink into and below the cranial bone as a consequence of skull bone growth, thereby threatening the brain. See, e.g., J. Fearon et al., Plast. Reconstr. Surg. 4 (1995) 634–637. Therefore, it is generally recommended that non-functional implants should be eventually removed, at least in growing individuals. See C. Lindqvist, Brit. J. Oral Maxillofac. Surg. 33 (1995) p. 69–70.

Especially in maxillofacial and in cranial surgery, metallic mini plates are popular for use. See e.g. W. Muhlbauer et al., Clin. Plast. Surg. 14 (1987) 101–111; A. Sadove and B. Eppleg, Ann. Plast. Surg. 27 (1991) 36–43; R. Suuronen, Biodegradable Self-reinforced Polylactide Plates and Screws in the Fixation of Osteotomies in the Mandible, Doctoral Thesis, Helsinki University, Helsinki, 1992, p. 16 and references therein. Mini plates are small, thin, narrow plates, which have holes for screw fixation. They are typically located perpendicularly over a bone fracture to affix the bone mass on either side of the fracture to each other. Typical geometries of mini plates are described e.g. in U.S. Pat. No. 5,290,281 at FIGS. 6A–6F.

The main advantage of metallic plates (like titanium, stainless steel and cobalt chrome molybdenum plates), is that they are strong, tough and ductile so that they can be deformed or shaped at room temperature in an operating room, either by hand or with special intruments, to a form corresponding to the surface topography of the bone to be fixed. In this way, the plate can be fixed flush on the bone surface to which the plate is applied.

In light of the above shortcomings of metallic plates, however, bioabsorbable plates have been developed for fracture fixation. Longitudinal, six-hole plates were developed for orthopaedic animal studies. See Eitenmüller et al. (European Congress on Biomaterials, Abstracts, Instituto Rizzoli, Bologna, 1986, p. 94). However, because of their inadequate strength, some of the plates were broken in animal experiments involving fracture fixation.

A special advantage of bioabsorbable plates is that they can be provided with openings for the insertion therethrough of surgical fasteners (like screws), while allowing means to permit the formation of additional fastener openings therethrough during a surgical procedure at the surgeon's discretion, as has been described in European Patent specification EP 0 449 867 B1.

Some bioabsorbable plates can be deformed (bended) permanently and safely only at elevated temperatures - above their glass transition temperature ($T_g$)—as has been described e.g. in EP 0 449 867 B1 and in U.S. Pat. No. 5,569,250. Below their $T_g$ such plates are brittle and break easily when deformed. Only at temperatures above $T_g$ does the molecular structure of such plates have enough mobility to allow shaping (e.g. bending), without the risk of breaking.

K. Bessho et al., J. Oral. Maxillofac. Surg. 55 (1997) 941–945 describes a bioabsorbable poly-L-lactide miniplate and screw system for osteosynthesis in oral and maxillofacial surgery. In order to be shaped, the plates of that reference must first be heated by immersion in a hot sterilized salt solution or by the application of hot air until they become plastic. Only after such heating can they be fitted to the surface of the bone.

EP 0 449 867 B1 describes a plate for the fixation of a bone fracture, osteotomy, arthrodesis, etc., said plate being intended to be fixed on bone with at least one fixation device, such as a screw, rod, clamp or corresponding device, wherein the plate comprises at least two essentially superimposed plates to provide a multilayer plate construction. The individual plates of said multilayer plate construction are elastic and flexible, so as to permit a change of form of said multilayer plate construction to substantially assume the shape of the bone surface in the operation conditions by means of an external force such as by hand and/or by bending instrument directed to said multilayer plate construction, whereby each individual plate assumes the position of its own with respect to other individual plates by differential motion along the respective surfaces of coinciding plates.

U.S. patent application Ser. No. 09/036,259 describes a bioabsorbable (bioresorbable or biodegradable), self-reinforced and/or oriented osteosynthesis plate which is strong, tough, and does not produce a substantial inflammatory response. The plate can be deformed, yet is dimensionally stable at temperatures below the glass transition temperature ($T_g$) of the material from which the device is made (e.g. at room temperature), thereby facilitating shaping. Such a bioabsorbable osteosynthesis plate is also dimensionally stable in tissue conditions, when fixed on bone surface to facilitate non-problematic bone fracture healing.

However, the above descibed metallic or bioabsorbale plates are not osteopromoting (osteoconductive or osteoinductive), which means that they do not actively promote new bone formation. Therefore, a need exists for a bioabsorbable plate which is osteoconductive and/or osteoinductive.

Partial osteoconductivity or osteoinductivity can be included into bioabsorbable plates by mixing osteoconductive or osteoinductive ceramic particles or fibers (made, e.g., of bioactive glass, of calcium phosphate or of hydroxyapatite) into a polymer matrix. Such materials are described e.g. in U.S. patent application Ser. No. 09/036, 259. Osteoinductive properties can also be achieved, e.g., by mixing bone morphogenic proteins or osteoinductive demineralized bone into a polymer matrix.

However, in the materials described above, only a part of the plate surface can be osteoconductive or osteoinductive, because the osteopromoting particles and/or fibers can be mixed with the polymer matrix only in a limited amount, typically up to 40 wt-%. Because ceramic materials are typically 2–3 times heavier than polymers, this means that, in practice, the ceramic particle or fiber phase, in the materials mentioned above, cover only about 20% of the surface of the plate, at a maximum.

SUMMARY OF THE INVENTION

In this invention, the osteoconductive and/or osteoinductive character of bioabsorbable polymeric or composite plates is improved significantly by coating at least one surface of the plate with osteoconductive and/or osteoinductive (i.e., osteopromoting) particles or fibers or fiber fabric.

Accordingly, the present invention describes bioabsorbable materials and implants, like plates, that have at least one surface with an osteopromoting coating of ceramic or organic particles or fibers or fiber fabric, which coating additionally intensifies, guides and improves new bone formation. The osteosynthesis plate of the present invention includes an elongated section having a top face and a bottom face, which elongated section is shaped to traverse a fracture site or osteotomy site for subsequent fixation to an adjacent bone. The osteosynthesis plate further includes either on its top face or on its bottom face or on both faces an osteopromoting coating formed of ceramic or organic particles or fibers or fiber fabric. The osteosynthesis plate further may include a plurality of fastener openings disposed between the top face and bottom face to allow the traverse of a plurality of surgical fasteners therethrough. The osteosynthesis plate further may include areas disposed upon the elongated section to permit the formation of additional fastener openings therethrough during a surgical procedure at the discretion of the surgeon.

One advantage of the present invention is that it provides a biocompatible implant, like a plate, of sufficient strength to securely affix a plurality of adjacent bone portions and additionally to improve new bone formation along at least one osteoconductive and/or osteoinductive plate surface. Preferably, the biocompatible implant is bioabsorbable over a desired period of time without generating a substantial inflammatory response.

In a preferred embodiment, the bioabsorbable plates can be deformed either at room temperature or at an elevated temperature, and substantially retain their deformed (shaped) form in vivo so that they, e.g., keep bone fragments essentially in the desired position to facilitate bone fracture healing and/or new bone formation. In another preferred embodiment, the plates of the present invention are low-profile and oriented (either uniaxially or biaxially) to improve their strength characteristics, so that they are strong, yet deformable. Such oriented osteosynthesis plates of the present invention may be repeatedly deformed and returned to their original configuration at room temperature in order to contour the osteosynthesis plate precisely to a desired configuration through successive iterations.

The present invention also includes bioabsorbable fixation devices or surgical fasteners, like bone screws, that are capable of being inserted through fastener openings disposed within the osteosynthesis plates of the present invention. As such, the present invention contemplates a bone stabilization device including a bioabsorbable osteosynthesis plate and one or more bioabsorbable surgical fasteners.

The present invention also provides a method for forming a biocompatible, bioabsorbable, osteopromoting osteosynthesis plate, including the steps of forming a sheet, optionally orienting the sheet, either uniaxially or biaxially, coating at least one surface of the sheet with an osteopromoting coating, and forming an osteosynthesis plate from the sheet.

The present invention is also directed to a method for securing a plurality of adjacent bone portions, including the steps of providing a bioabsorbable, biocompatible, osteopromoting, osteosynthesis plate, positioning the osteosynthesis plate upon a plurality of adjacent bone portions, providing a plurality of surgical fasteners for securing the osteosynthesis plate to the adjacent bone portions, positioning the plurality of surgical fasteners through the osteosynthesis plate and securing the plurality of surgical fasteners into the adjacent bone portions.

BRIEF DESCRIPTION OF THE DRAWINGS

Other advantages of the present invention will become apparent to one skilled in the art upon reading the following specification and the following drawings.

DESCRIPTION OF THE PREFERRED EMBODIMENTS

For the purpose of promoting and understanding of the principles of the invention, reference will now be made to the preferred embodiments of the present invention. It will nevertheless be understood that no limitation of the scope of the invention is thereby intended.

Figure 1:
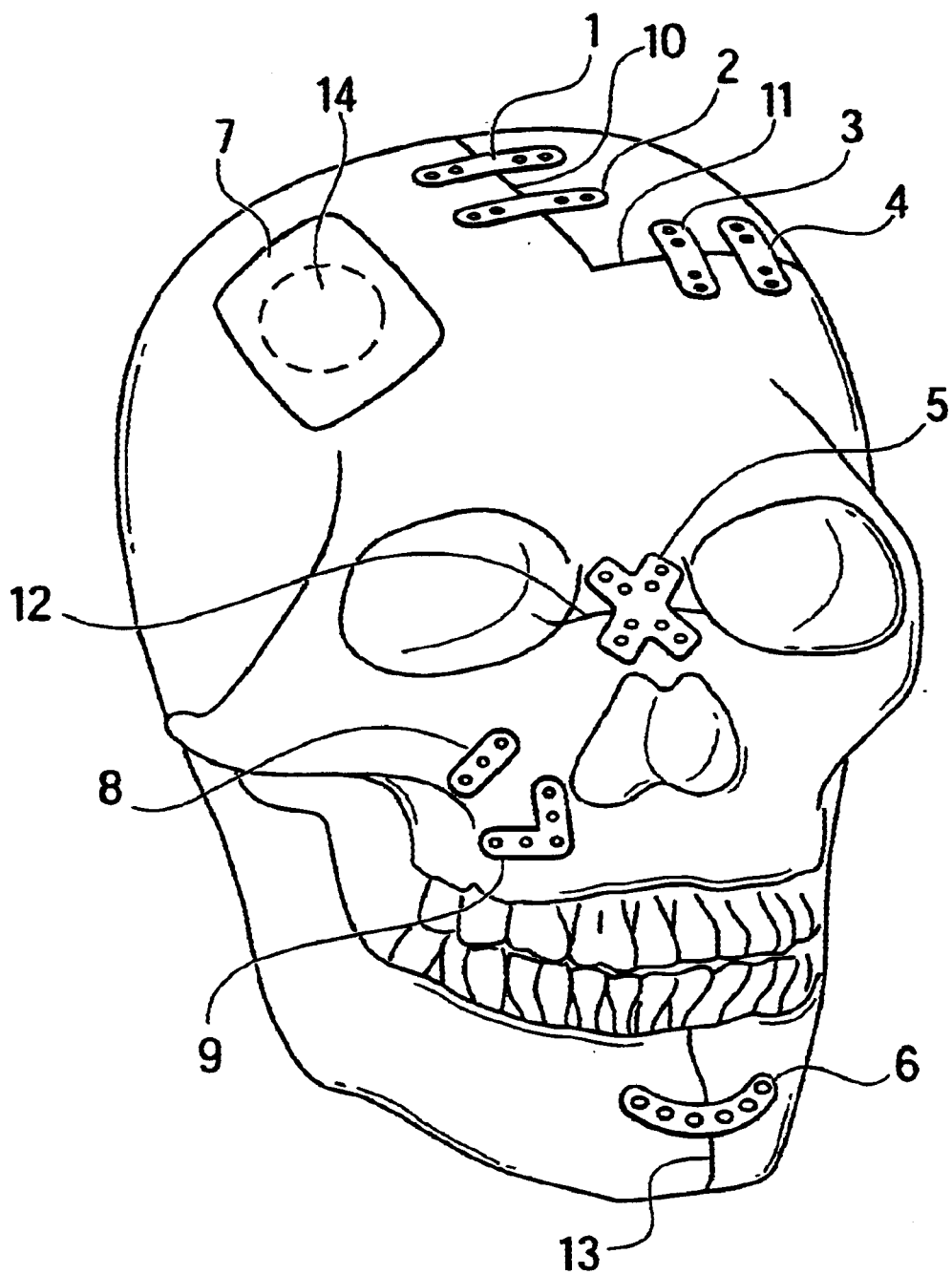
FIG. 1 is a perspective view of a plurality of bioabsorbable, osteodonductive and/or osteoinductive osteosynthesis plates according the present invention, shown in association with the repair of multiple cranio maxillofacial or mandibular fractures or bone defects or reconstruction to include pediatric and orthognatic areas.

Referring to FIG. 1, there are shown biocompatible, bioabsorbable osteosynthesis plates 1–9 according to preferred embodiments of the present invention. Osteopromoting osteosynthesis plates 1–6 are shown as being disposed over bone fractures 10–13, plate 7 is shown as being disposed over a hole (gap) 14 in skull bone, while plates 8 and 9 are shown as being disposed in position for facial reconstruction. It will be appreciated that the biocompatible, bioabsorbable osteosynthesis plates of this invention, like plates 1–9, may be of any size or shape as will be hereinafter discussed. Further, the biocompatible osteoconductive and/or osteoinductive osteosynthesis plates 1–9 may also be deformable and rigid at a first thermochemical state, like in operating room conditions. "A thermochemical state", as used here, is defined according to U.S. Pat. No. 5,569,250 as a combination of thermal and chemical conditions resulting from exposure to certain thermal and chemical environments, like room temperature and operating room atmosphere, respectively. Although one type of change in thermochemical state occurs by a change of temperature alone, changes in thermochemical state of (optionally uni- and/or biaxially oriented) biocompatible implants of the present invention should be understood as not limited only to changes in temperature. Preferably, the biocompatible, bioabsorbable osteopromoting osteosynthesis plates of the present invention are relatively rigid at both room temperature and at human body temperature and they are optionally deformable at temperatures (like at room temperature) below $T_g$ of the material from which the biocompatible osteosynthesis plates are made. In such advantageous cases, there is no need to heat the plates of this invention to temperatures above $T_g$ of the material in order to bend the plates.

Osteopromoting osteosynthesis plates made of bioabsorbable materials in the manner discussed below will retain a substantial proportion of their strength after the first several weeks or months in vivo, when this strength must be relatively high. Such osteosynthesis plates may be made of partially crystalline or of non-crystalline (amorphous) materials. In a preferred embodiment, osteosynthesis plates of the present invention are capable of stabilizing a plurality of bone portions for a period (of) from one to several months following implantation, and yet they will be completely resorbed after one year or several years following implantation, depending on such factors as chemical composition and/or molar mass of the bioabsorbable polymeric material and of the coating material, implant size and geometry or the position of the implant in the human body. Accordingly, the resorption time can be tailored to be fast or slow. Slow resorption is advantageous in the case of slowly healing fractures, osteotomies or bone gaps or holes and a relatively fast resorption of the bioabsorbable material reduces the unwanted cosmetic appearance as well as growth restriction in pediatric patients.

It will be appreciated that the biocompatible, bioabsorbable, osteopromoting osteosynthesis plate of the present invention may be of a variety of sizes and/or shapes as hereinafter discussed and may also be of a bioresorbable material of different origins.

Figure 2A:
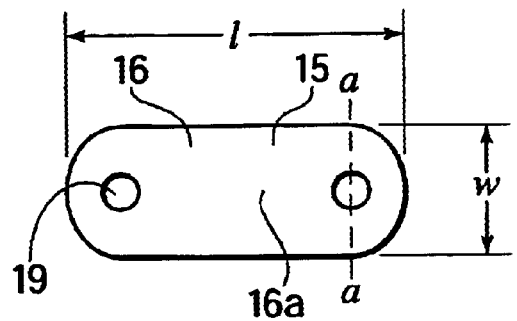
FIGS. 2A–2D are top views of osteosynthesis plates according to the teachings of some embodiments of the present invention.

Referring to FIGS. 2A–2D and 3A–3C, several osteopromoting osteosynthesis plates according to the invention are described. FIG. 2A shows a plate in the form of a flat plate 15. The flat plate 15 includes an elongated section 16 having a top face and a bottom face (not shown). The flat plate 15 is further shown to include a plurality of fastener openings 19 that are of substantially cylindrical shape and are disposed between the top face and the bottom face. The fastener openings 19 allow the traverse of surgical fasteners for securing the flat plate 15 to a bone surface (not shown) to which the flat plate 15 may be applied. It will be appreciated, however, that the fastener openings 19 do not have to be present if the surgeon uses other means for securing the flat plate 15 to bone. Preferably, the flat plate 15 is applied to a bone surface such that the plane or contour formed by the bottom face is substantially flush with the bone surface to which the flat plate 15 is applied.

The flat plate 15 further includes an area disposed upon the elongated section 16 to permit the formation of additional fastener openings therethrough at a plurality of different positions during a surgical procedure. In a typical embodiment, this is provided by having the elongated section 16 include a mid-portion 16a which is disposed between the fastener openings 19 and having substantially the same width as the portion of the plate 15, which is adjacent to the fastener openings 19. Accordingly, the surgeon is able to drill through the mid-portion 16A to form additional fastener openings as the particular application may require. It is natural that the arrangement of fastener openings and additional fastener openings can have different embodiments depending on the condition of the bone being treated, the type of fracture present, etc. Other types of fastener opening and additional fastener opening combinations known in the art are shown in, e.g. in EP 0 449 867 B1.

Figure 3A:
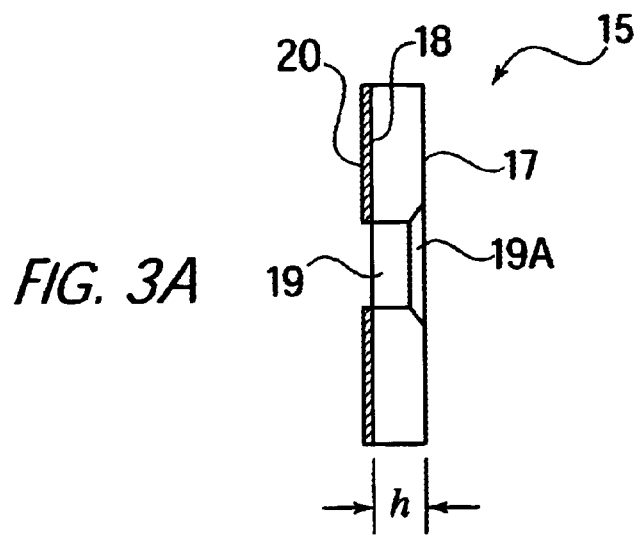
FIGS. 3A–3C are cross-sectional views of the osteosynthesis plates of FIG. 2A along line a—a according to the teachings of preferred embodiments of the present invention.
Figure 3B:
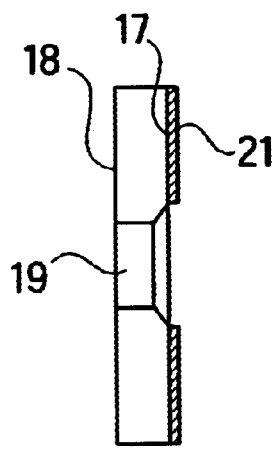
Figure 3C:
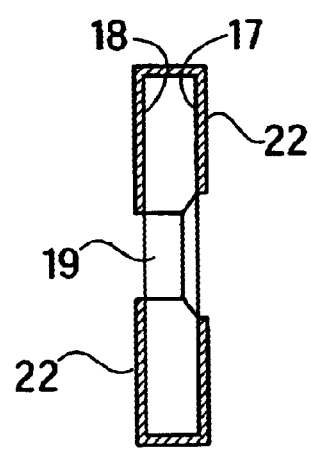

According to FIGS. 3A–3C, the osteosynthesis plates of the invention have at least on their bottom face 18 or top face 17 an osteopromoting coating. According to FIG. 3A the osteopromoting layer (coating) 20 is on the bottom face 18 of the plate 15. According to FIG. 3B the coating 21 is on the top face 17 and according to FIG. 3C the coating 22 is on both the top face 17 and bottom face 18 of the osteosynthesis plate. It is also possible that the sides and/or end surfaces of the plate could have the osteoconductive and/or osteoinductive coating.

According to an advantageous embodiment of the present invention, the flat plate 15 has a "low profile" construction, i.e., is thin so as to minimally protrude above the bone surface to which it is applied. In this regard, the term "low profile" will be used to refer to a construction in which the width is greater than about four to six times the height of the plate 15. For example, the plate 15 may typically have a width ("w") of 4–8 mm, a length ("l") of between about 10 mm to 80 mm and a height ("h") (thickness) of about 0.3 mm to 2 mm, as shown in FIGS. 2 and 3. The flat plate 15 is preferably bioabsorbable, so that the flat plate 15 may be resorbed into the body through processes well known to those skilled in the art over a desired period of time.

Figure 4A:
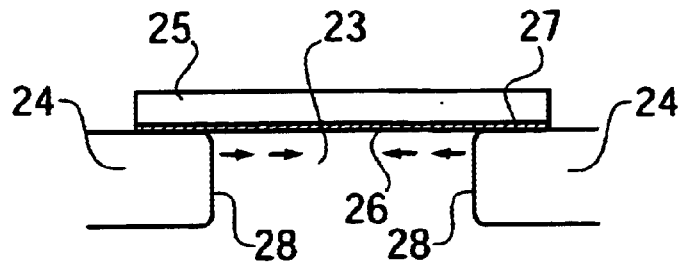
FIGS. 4A–4D show schematically the progressive healing of a bone gap below the osteoconductive and/or osteoinductive plate of the invention. After bone healing the plate absorbs, and the bone remains, according to FIG. 4E.
Figure 4B:
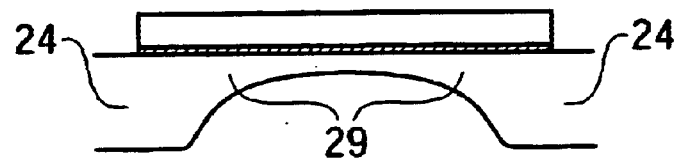
Figure 4C:
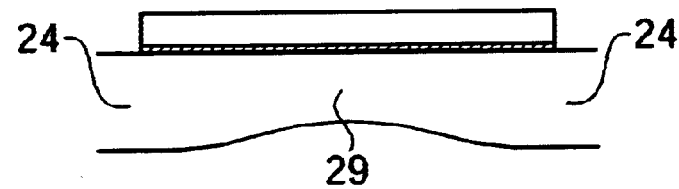
Figure 4D:
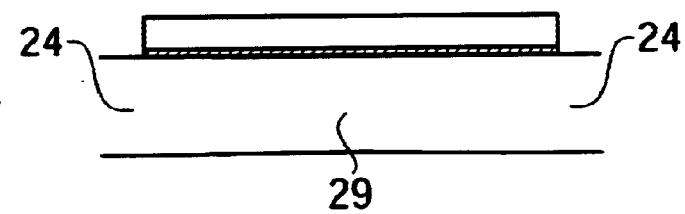
Figure 4E:
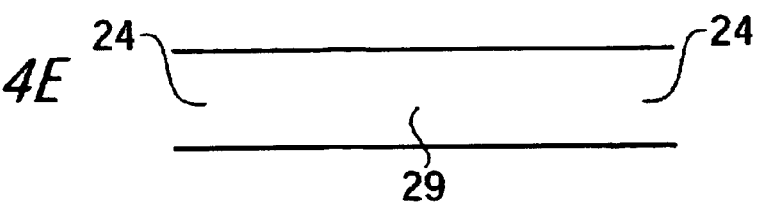

The osteosynthesis plate of the present invention is characterized by its ability to improve and accelerate fracture healing and/or new bone formation into bone defects (e.g. gaps or holes) by means of the osteopromoting coating on at least one surface of the plate, as is described e.g. in FIGS. 3A–3C. When the osteosynthesis plate of the invention is located (fixed) over a bone gap or fracture, the osteopromoting coating intensifies and guides the new bone formation over the gap or fracture, as can be seen from the schematic FIGS. 4A–4E. According to FIG. 4A a gap 23 in a bone 24 is covered with an osteosynthesis plate 25, which has an osteopromoting coating 26 on its bottom face 27. The new bone formation proceeds from the edges 28 of the gap 23 into the gap 23 as is shown shematically with small arrows in FIG. 4A. The gap 23 fills up progressively with the new bone 29, as is seen schematically in FIGS. 4B–4D. The osteopromoting layer 26 accelerates and improves the new bone 29 formation so that more rapid and better healing is obtained as compared to prior art plates. During and after bone healing the osteopromoting plate 25 and its coating 26 disappear by bioabsorption so that finally, according to FIG. 4E, the healed bone 24, 29, 24 is left and there are no risks of long-term implant-related complications.

In one preferred embodiment of the present inveniton, the coating 26 is thicker (e.g. 3–10 mm thick) in the area of gap 23 than in the area between the bone 24 and plate 25 (where the coating can be typically 0.1–1 mm thick). In such a case the new bone grows rapidly into the thick coating in the gap 23 filling it rapidly and effectively with new bone.

If also the upper surface of the plate 25 (and also optionally the sides and ends of the plate 25) contain(s) the coating 26, the new bone grows rapidly also over the plate 25, burying it into the new bone, where it later bioabsorbs and will be replaced with new tissue, like bone.

In yet another preferred embodiment of the present invention, the coated osteosynthesis plate may be deformed without heating it above $T_g$ of the plate material. Thus, during a surgical procedure, it may be easily conformed to the contour of the bone surface to which it is applied. This feature is especially useful in the surgical repair of bone surfaces having high curvatures, including the maxillofacial bones of the craniofacial skeleton. During such deformation, the coated plate is deformed by manipulating the plate by hand or with manipulating devices, in a first thermochemical state, i.e. in the operating room conditions during a surgical operation. Accordingly, there is no need, before its deformation, to elevate that plate to a higher temperature, using e.g. a heating device, as is,needed e.g. in U.S. Pat. No. 5,569,250. The deformed plate of the invention will then be placed into the second thermochemical state when fixed on bone in the body to secure the bone fracture. More preferably, because the flat uni- and/or biaxially oriented osteosynthesis plate is formed by a method which causes the plate to be deformable, ductile, rigid and dimensionally stable under operating room conditions, in the first thermochemical state, the coated plate is able to return to its original configuration upon deforming it again in operating room conditions. As such, it will be appreciated that this ability allows the coated plate to be repeatedly deformed and returned to its original configuration, thus allowing for successive attempts by a surgeon during a surgical procedure to conform the coated plate as closely as possible to the contours of the bone surface to which the coated plate will be applied. These successive deformations can be performed conveniently and rapidly in an operating room without heating and cooling conversions, which are necessary for the bending of prior art plates, like those of U.S. Pat. No. 5,569,250.

The formation of additional fastener openings through the coated plates of certain embodiments of the present invention may be accomplished by simply drilling through the material from which the coated plate is made. Such drilling may be performed through means well known to those skilled in the art. The surgical fasteners, e.g. such as biocompatible bioresorbable bone screws, may be constructed of the same polymer material as the coated plate, or may alternatively be made of another bioabsorbable material.

In a preferred embodiment of the present invention, the coated bottom face of the plate is in substantially flush contact with the bone surface to which it is applied. A plurality of fasteners (not shown) may be disposed through the plate for securing it into position, with the head of the surgical fastener being tightened against the top face of the coated plate. This arrangement results in a secure relationship between the coated plate and the underlying bone surface. According to another advantageous embodiment of the present invention, the fastener opening 19 (see FIGS. 2 and 3) is conically widened from its opening end on the top face 17 so that it forms a countersink 19a on the top face 17.

In addition to a simple plate with a constant width w and one or several fastener openings (as is seen e.g. in FIGS. 2A and 2B) the coated bioabsorbable plates of the invention can have such a design that the width of the plate in the area between two fastener openings is smaller than the width of plate around the fastener openings (or the width of the area into which additional fastening openings can be drilled). FIGS. 2C–2D illustrate such plates. A special advantage of the plates of FIG. 2C–2D is that these plates can be deformed also in the flat plane of the plate, in addition to bending and torsional deformations, which are typical for plates having a constant width, like those of FIGS. 2A–2B.

Figure 5:
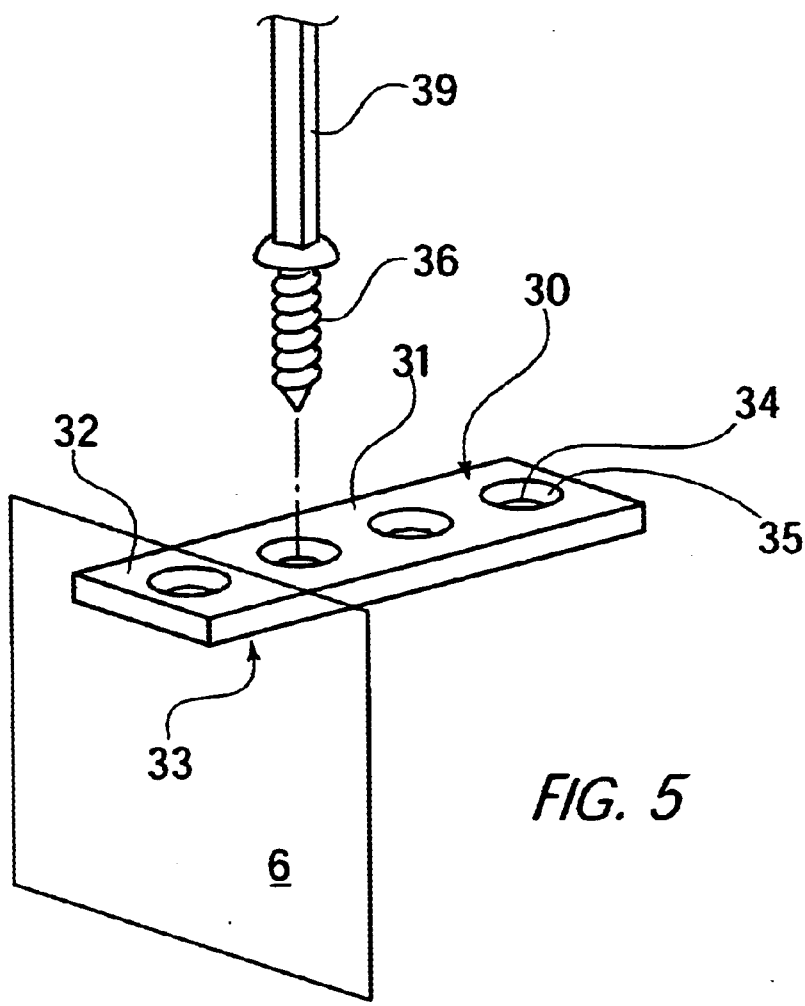
FIG. 5 is a perspective view illustrating an osteoconductive and/or osteoinductive (optionally uni- and/or biaxially oriented) osteosynthesis plate in combination with a bone screw positioned in a relative elevated position for insertion within a fastener opening of the osteosynthesis plate.
Figure 6:
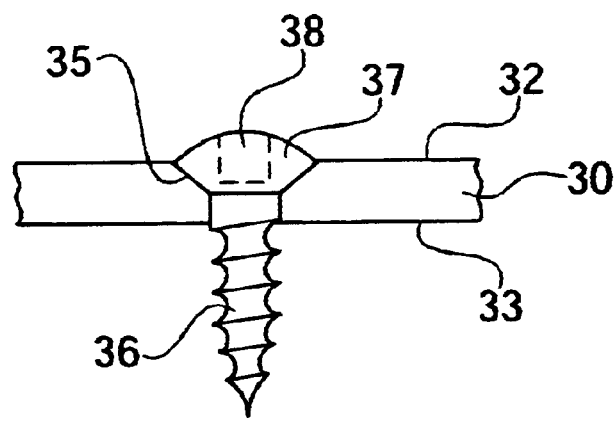
FIG. 6 is a cross-sectional view of the osteosynthesis plate shown in FIG. 5 along plane b with a bone screw disposed within a fastener opening of the osteosynthesis plate.

Referring now to FIGS. 5 and 6, there is shown a biocompatible, coated osteosynthesis plate 30 according to a preferred embodiment of the present invention. FIG. 5 illustrates a perspective view of the osteosynthesis plate 30, which includes an elongated section 31 having a top face 32 and a bottom face 33, coated with an osteoconductive and/or osteoinductive layer (not shown). The flat, smooth-surfaced configuration of osteosynthesis plate is intended to render the plate 30 in a "low-profile" configuration. This is accomplished by making the elongated section 31 to be as thin as possible to accomplish the desired result without any protrusions which disadvantageously increase the thickness of the plates. Preferably, the width of the osteosynthesis plate 30 is greater than approximately four to six times the thickness of the plate. It has been determined that a minimum thickness of the plate is desirable for minimizing the amount of mass and the cross-section of the osteosynthesis plate 30, as well as providing the desired resorption time for a complete resorption of the osteosynthes plate into the body. It has also been determined that this principle, which involves the spreading of the mass of an osteosynthesis plate over a larger surface area, provides improved results in both reducing the cosmetic effect of implantation of these devices, as well as providing a more favorable time for resorption of the material due to smaller cross-sectional area.

According to an advantageous embodiment of the present invention, the osteosynthesis plate 30 is also characterized by its ability to be deformed during a surgical procedure at room temperature so that it may be easily and efficiently conformed to the contour of the bone surface to which it is applied. This feature is especially useful in the surgical repair of bone surfaces having high curvatures, including the maxillofacial bones of the skull, as previously described.

The osteosynthesis plate 30 also includes a plurality of fastener openings 34 which are disposed between the top face 32 and the bottom face 33. As before, the fastener openings 34 allow the traverse of a plurality of surgical fasteners therethrough. The fastener openings 34 may each be further provided with a countersink 35, which is capable of accepting a preferably correspondingly shaped portion of a head of a surgical fastener. As such, the countersink 35 may be oriented in a substantially hemispherical configuration, a substantially frustoconical configuration, or in any other configuration suitable for the particular need.

FIGS. 5 and 6 also illustrate a surgical fastener in the form of a bone screw 36, located above the surface of the osteosynthesis plate 30 in FIG. 5, and located in its fully inserted position in FIG. 6. When fully inserted, the head 37 of the bone screw 36 may be mainly or substantially contained below the top face 32 of the plate 30 thereby complementing the low-profile configuration of the osteosynthesis plate 30. The bone screw 36 may be made from the same or different biocompatible and bioabsorbable materials as the osteosynthesis plate 30, thereby providing a fully bioresorbable bone stabilization device.

As is illustrated in FIGS. 5 and 6, when the surgical fastener is provided in the form of a bioresorbable bone screw 36, head 37 of the bone screw 36 includes a fastener socket 38 into which the tip of the installation tool, like a screwdriver 39, can be pushed. The screwdriver 39 is used for engaging the bone screw 36 for insertion within a fastener opening 34 and subsequent rotation of the bone screw 36 while threading into an underlying bone structure. The cross-section of the socket 38 can be e.g. triangular, quadrangular (like in FIG. 5), hexagonal, etc. It will be appreciated that the socket 38 and the corresponding tip of a screwdriver 39 may be shaped in any suitable configuration to match each other.

Figure 7A:
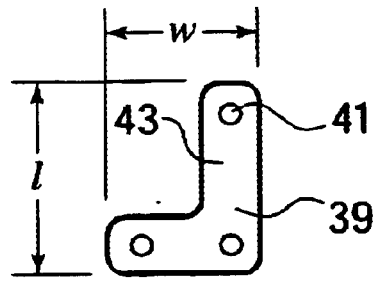
FIGS. 7A–7J are top views of some other geometries of osteosynthesis plates according to the teachings of the present invention.
Figure 7B:
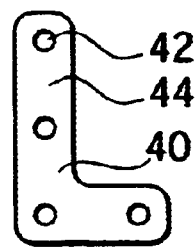
Figure 7C:
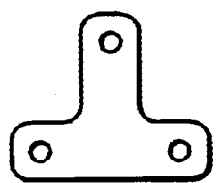
Figure 7D:
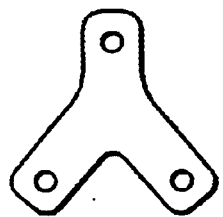
Figure 7E:
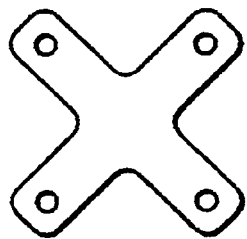
Figure 7F:
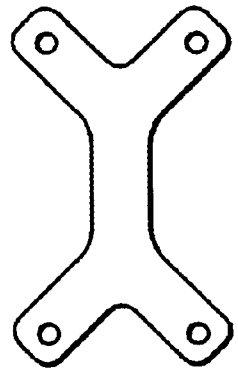
Figure 7G:
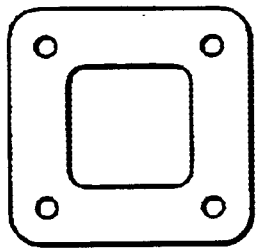
Figure 7H:
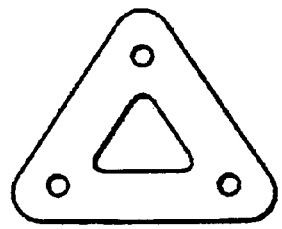
Figure 7I:
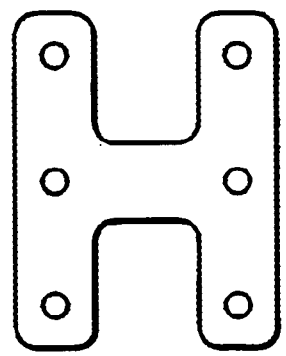

Referring to FIGS. 7A through 7J, there are shown a plurality of configurations of flat osteosynthesis plates according to the present invention. FIGS. 7A and 7B show L-plates 39 and 40 according to embodiments of the present invention. The L-plates 39 and 40 are further shown to include a plurality of fastener openings 41 and 42 disposed upon the elongated sections 43 and 44 near the terminal portions and at the corner sections of the elongated sections. Preferably, L-plate 39 has a width w of about 12 mm, a length (l) of about 20 mm, and a thickness of about 0.5–1.0 mm.

Figure 7J:
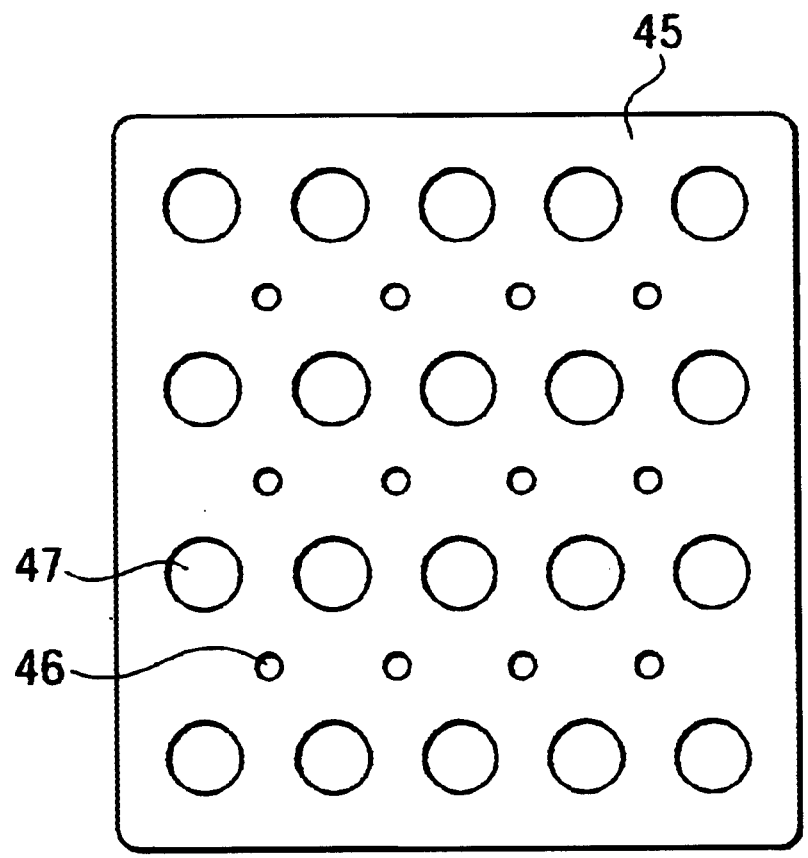

FIGS. 7C–7I show other preferable configurations of plates, like a T-plate (7C), Y-plate (7D), X-plates (7E and 7F), square plate (7G), triangle plate (7H) and H-plate (7I). All of these plates may include a plurality of holes for fasteners, depending on the size and use indications of the plate. FIG. 7J shows a mesh-plate 45 with a plurality of smaller holes 46 for fastener fixation and bigger holes 47 to facilitate tissue healing through the plate 45 and to reduce the mass of the plate 45. It will be appreciated that the examples set forth in FIGS. 7A–7J are meant to be illustrative, and not a limitation, of the varieties of osteosynthesis plate shapes which may be constructed according to the present invention. In addition, it will be appreciated that any of the above osteosynthesis plates may be constructed to include areas disposed upon the elongated sections to permit the formation of additional fastener openings therethrough during a surgical procedure.

It will further be appreciated that these osteosynthesis plates may be constructed of any of the materials previously discussed, or may be constructed from other suitable materials. As before, it is preferred that any of the above osteosynthesis plates is constructed of a bioabsorbable (resorbable) material. Also as before, the bioabsorbable material may be combined in a bone stabilization device with bioabsorbable surgical fasteners, such as bone screws. The osteosynthesis plates of the present invention can be manufactured of thermoplastic bioabsorbable (resorbable or biodegradable)-polymers, copolymers, polymer alloys, or composites e.g. of poly-α-hydroxy acids and other aliphatic bioabsorbable polyesters, polyanhydrides, polyorthoesters, polyorganophosphatzenes, tyrosine polymers, like tyrosine polycarbonates, and other bioabsorbable polymers disclosed in numerous publications, e.g. in S. Vainionpääet al. , Prog. Polym. Sci., 14 (1989) 679–716, FI Patent No. 952884, FI Patent No. 955547 and WO-90/04982, EP 0449867 B1, U.S. Pat. No. 5,569,250, S. I. Ertel et al., J. Biomed. Mater. Res., 29 (1995) 1337–1348 as well as in the reference publications mentioned in the aforementioned publications.

Implants in accordance with the present invention can be manufactured of bioabsorbable polymers by using one polymer or a polymer alloy. The implants can also be reinforced by reinforcing the material with fibers manufactured of a bioabsorbable polymer or of a polymer alloy, or with bioabsorbable or biodegradable glass fibers, such as β-tricalsiumphosphate fibers, bioactive glass fibers or CaM fibers. Ceramic powders can also be used as additives (fillers) in implants of the invention.

In a preferred embodiment of the present invention, the plates can also contain layered parts comprising a flexible outer layer, which is a surface layer improving the toughness of the implant and/or operating as a hydrolysis barrier, and a stiffer inner layer or core of the implant. To prepare such an embodiment, the implant can be coated with an outer layer having different chemical and mechanical properties (e.g., hydrolysis and strength retention) than the core of the implant. In such a case, an outer layer having greater resistance to hydrolysis than the implant's core can be used, enabling the implant (after insertion in a patient) to retain its strength and biodegrade more slowly than it would have without such an outer coating.

The osteopromoting coating of the osteosynthesis plates of the present invention can be manufactured of bone growth facilitating ceramic or organic materials. The most important such ceramic materials are:

Bioactive glasses as particles, fibers or fiber fabrics (see e.g. L. L. Hench, J.Biomed. Mater. Res., 41 (1998) p. 511–518 and D. L. Wheeler et al. J.Biomed. Mater. Res., 41 (1998) p. 527–533, and PTC/FI 96/00001), Sol-gel derived silica fibers, as described e.g. in German Patent 196 09 551.4 or in WO 97/45367 and Calcium phosphates, especially Hydroxyapatite (HA) (see e.g. U.S. Pat. No. 5,338,772 and L. L. Hench, J.Biomedical Materials Res. 41 (1998) p. 511–518).

The most important organic osteopromoting materials, suitable to be used as coating in the plates of the present invention, are cellulosis-based, bioabsorbable polymer-based and collagen-based materials. Especially collagen-based products are well known in surgical practice and are available as different products, like powders, short-fiber mixtures, non-woven fabrics etc. Nonlimiting example of collagen-based materials is e.g. Grafton® demineralized bone matrix (DBM) of Osteotech Inc. (Eatontown, N.J., USA).

According to an advantageous embodiment of the present invention, the cellulosis-, polymer-, ceramic- or glass- or collagen-based coating of the invention includes bioactive molecules which enhance the osteoconductive and/or osteoinductive or osteogenesis effect of the coating.

Demineralised bone is an example of a collagen-based product, including bone growth promoting proteins and showing osteoinductive activity (see e.g. R. M. Wilkins in "The First Combined Meeting, European Associations of Tissue Banks (EATB) and Musculo Skeletal Transplantation (EAMST)", Sept. 10–12, 1998, Turku, Finland,Program and Abstracts, p. 105).

Another example of osteoinductive collagen-based products is NOVOS-material of Stryker BIOTECH (Natic, Mass., USA) comprising osteoconductive type I bone collagen, which is enhanced by the presence of Osteogenic Protein-1 (OP-1). Another example is OSSIGEL-material of Orquest (Mountain View, Calif., USA)

Other organic osteoconductive and/or osteoinductive materials can be based e.g. on cellulose derivates or on synthetic organic bioabsorbable polymers which include bioactive molecules, like bone morphogenic proteins, growth factors or osteopromoting peptides.

It is natural that the materials and implants of the present invention can also contain various additives for facilitating the processability of the material (e.g. stabilizers, antioxidants or plasticizers) or for changing its properties (e.g. plasticizers or ceramic powder materials or biostable fibers, such as carbon) or for facilitating its treatment (e.g. colorants).

According to one advantageous embodiment of the present inveniton, the coating and/or also the polymeric plate material of the implant of the invention contains some other bioactive agent or agents, such as antibiotics, chemotherapeutic agents, agents activating healing of wounds, growth factor(s), bone morphogenic protein(s), anticoagulant (such as heparin), etc. Such bioactive plate materials are advantageous in clinical use, because they have, in addition to their mechanical effect, also biochemical, medical and other effects to facilitate tissue healing and/or regeneration.

A manufacturing procedure for making osteopromoting plates of the present invention follows:

First the polymer raw material (+optional additives and/or filler(s) and/or reinforcing fibers) in the form of a powder, flakes, pellets or granulate, etc., will be melted with a continuous process, like extrusion, or with a noncontinuous process, like injection molding or compression molding. The melted material will be cooled in a mold or after die extrusion so that it solidifies to an amorphous or partially crystalline (crystallinity typically 5–50%) plate or plate preform, like a cylindrical rod or bar, a flat balk with a rectangular cross-section, or a sheet stock. Cooling can be done inside a mold in injection molding and in compression molding techniques. In extrusion, the preform will be formed from material melt in a die and the preform will be led onto a special cooling belt or into a cooling solution to make a solid preform. The coating of the plate preform can be applied during extrusion directly to the surface of the cooling or cooled preform by scattering the coating powder or fibers on it and or by pressing the coating material on the surface of the cooling preform The melt molded non-coated plates and extruded plate preforms can be coated after melt-molding with the osteoconductive and/or osteoinductive layer at least on one surface of the plate or preform. Before coating, the plates and preforms can also be oriented and self-reinforced with uni- and/or biaxial solid state deformation processes to transform the material to a state that is substantially rigid and substantially deformable at the room temperature conditions of a surgical operation.

The coating of the osteosynthesis plate surface with ceramic or organic particle powder, short fibers, long fibers or fiber fabrics ("coating") can be accomplished by several different methods. The plate surface can be covered with coating and heat and pressure can be applied to press the particles partially into the plate structure and/or to stick them on the plate structure. The same process can be used with short ceramic or organic fibers. Also, ceramic or organic fiber fabrics, like woven and non woven fabrics, can be fixed on a plate surface with heat and pressure, provided that the fiber material is heat-resistant enough.

According to an advantageous embodiment of the present invention, the coating is performed with plasma spraying so that the finely dispersed ceramic melt droplets are blown against the plate surface so that the hot droplets or solid particles hit the plate surface and adhere onto it. Also, other physical coating methods, like sputtering, can be applied. In sputtering, high energy radiation hits the ceramic target, which releases small particles that are guided to contact the plate surface, where the particle adhere.

Organic coatings, such as collagen-based or synthetic bioabsorbable polymer-based materials, which have high thermal sensitivity may be applied to osteosynthesis plates of the present invention e.g. with low-temperature glueing methods or with solvent treatment methods.

Before coating, the surface of the plate can be dissolved and/or eroded and/or softened and/or made sticky by applying a suitable organic solution to it which dissolves and/or swells the surface. The organic solution can also contain dispersed and/or dissolved bioactive organic additives, like pharmaceutical(s), drug(s), growth factors, etc., which can have advantageous effects in tissue healing and regeneration. Thereafter, the organic coating, like synthetic polymer or collagen-based product, in the form of powder, short fiber mixture, non-woven fabric, woven or knitted fabric, etc., can be pressed against the sticky surface onto which it adheres. Then, the dissolving and/or swelling solvent can be evaporated at room temperature or at a slightly elevated temperature or even at low temperatures (below room temperature) (optionally in a (high) vacuum).

It is also possible to apply on a plate surface a suitable solution of a bioabsorbable polymer, which solution acts as a glue. After applying the glueing solution, the organic coating can be pressed against the glue surface, where it adheres. Thereafter the solvent of the glue can be evaporated, as above.

Instead of solution glueing, it is also possible to use low-temperature melt-glueing to bind the organic coating, e.g. the synthetic polymer-, cellulosis- or collagen-based layer, on the osteosynthesis plate. Even if many bioabsorbable polymeric materials, suitable as osteosynthesis plates, become sticky only at temperatures well above 100° C., there are also low temperature melting bioabsorbable polymers and copolymers, polymer alloys or polymer+oligomer mixtures or plasticized polymers or mixtures which melt or become sticky at temperatures well below 100° C. Such polymers and copolymers can be used as melt adhesives to bind the synthetic polymer-, cellulosis- or collagen-based layer to the plate surface. Accordingly, the bioabsorbable polymer or copolymer etc., which becomes sticky or melts at a temperature well below 100° C. (e.g. between 40° C.–50° C.), will be applied on the plate surface and the organic coating will be pressed on the melt adhesive polymer layer before it solidifies. Another low temperature melt adhesive technique is to stack up the plate, the bioabsorbable melt adhesive film and the organic coating layer on each other and to compress the components together by applying pressure and careful heating so that the bioabsorbable melt adhesive film becomes sticky or melts and glues the plate surface and the organic coating layer together.

These coating techniques can be performed on injection molded or compression molded or on extruded plates, as well as on oriented or self-reinforced flat plate preforms (sheet stock).

Orientation and self-reinforcing in solid state are methods to increase the strength, modulus, ductility and plastic deformation capacity of bioabsorbable materials and implants. Such methods are described e.g. in publications: P. Törmälä, Clin.Mater. 10 (1992) 29–34P. Törmälä, et al., Proc. Instn Mech. Engrs. 212 (1998) 101–111. Drawing through a heated die (die drawing) is the most common method to orient or self-reinforce bioabsorbable polymer billets.

The billet may also be forced through the die by pushing the billet mechanically with a piston through the die (ram extrusion) or by pushing the billet through the die with hydrostatic pressure (hydrostatic extrusion) (see e.g. N. Inoue, in Hydrostatic Extrusion, N. Inoue and M. Nishihara (eds.), Elsevier Applied Science Publishers, Barbing, England, 1985, p. 333–362). It is also possible to create orientation by shearing the flat billet between two flat plates which glide in relation to each other and approach each other at the same time, causing the orientation and/or selfreinforcing to form in the plate material. It is also possible to deform the billet in a compression molding device between flat plates which are pushed towards each other so that the billet deforms biaxially between the plates and attains the desired final thickness. The deformation can be done also by rolling the rod-like or plate-like preform between rollers, which flatten the preform to the desired thickness, biaxially orienting the material at the same time. It is natural that these different deformation methods can be combined. E.g. hydrostatic deformation can be combined with die drawing or rolling can be combined with drawing, e.g. by using two pairs of rollers after each other, which rollers have different rolling speeds, etc.

The billet and/or die compression plates or rolls can be heated to the desired deformation temperature with electrical heating or with a suitable heating medium, like a gas or heating liquid. The heating can be done also with microwaves or by ultrasonic means to accelerate the heating of the billet. Regardless of the deformation method, the purpose of the solid state deformation is the orientation of the material so that the material is transformed from a weak and brittle material to a strong and ductile material.

Following the coating step, osteosynthesis plates, such as the flat plates of FIGS. 1–7, can be formed by machining or stamping the plate and the fastener opening(s) and the countersink(s). Following forming, the plates of the present invention may be finished to provide clean surfaces and an aesthetic appearance. This is accomplished by trimming with suitable trimming devices, such as knives or cutting blades or grinding devices, or may also be accomplished by an additional stamping step. Once the removal of surface and/or side irregularities has occurred, the substantially completed product is subjected to cleaning with a suitable cleaning agent, like ethyl alcohol-water mixture. Mechanical agitation and ultrasonic agitation can be used to facilitate the cleaning. In this step, the outer surface of the osteosynthesis plate is cleaned of fingerprints, soils and oils resulting from possible contact with human hands and other surfaces, as well as impurities which may collect on the surfaces. Care must be taken to avoid the damaging of the coating during finishing. Finally, the plates are dried, packed and sterilizided using standard methods.

The above-mentioned steps of manufacturing an osteosynthesis plate of the present invention may further include additional steps, such as for quality control purposes. These additional steps may include visual or other types of inspections or testing during or between the various steps, as well as final product inspection including chemical and/or physical testing and characterization steps and other quality control testing.

The method for securing a plurality of adjacent bone portions according to the present invention will now be described. The first step of this method includes providing a sterile, coated biocompatible osteosynthesis plate, such as the osteosynthesis plates of FIGS. 1–7. This is achieved by opening the plate package and supplying the sterile plate to the surgeon. Depending on the surface topography of the bone to be fixed the surgeon then shapes (deforms), if necessary, the osteosynthesis plate (optionally heating it before shaping, if necessary), to a first desired configuration by hand or with special manipulation instruments. The surgeon can then conveniently test the shaped plate by pressing the plate gently against the bone to be fixed and if the first desired configuration is not sufficient for completing the surgical requirements, the surgeon can reshape the osteosynthesis plate to a second desired configuration.

It will be appreciated that the method of the present invention further includes the capability for repetitively reshaping, at constant operating room temperature, or at an elevated temperature, the osteosynthesis plate to successive desired configurations and ceasing reshaping the osteosynthesis plate when a desired final configuration of the osteosynthesis plate has been achieved.

The osteosynthesis plate is then positioned upon a plurality of adjacent bone portions. According to an advantageous embodiment, the osteoconductive and/or osteoinductive, coated surface will be located against bone surface, as is described e.g. in FIGS. 4A–4D. A plurality of surgical fasteners are then provided for enhancing a fixed relation between the osteosynthesis plate and at least one adjacent bone portion. A plurality of surgical fasteners are then positioned within a plurality of fastener openings located upon the osteosynthesis plate. The plurality of surgical fasteners are then secured to the adjacent bone portions, thereby engaging the biocompatible osteosynthesis plate with each bone portion.

This method may further include the additional steps of creating at least one additional fastener opening through the osteosynthesis plate at a location adjacent to at least one bone portion, positioning an additional surgical fastener within each additional fastener opening, and substantially securing each additional surgical fastener into each bone portion, thereby enhancing an engagement of the osteosynthesis plate with each bone portion. This method may also include the step of engaging the osteosynthesis plate with at least one adjacent osteosynthesis plate.

The principles of the present invention described broadly above will now be described with reference to the following specific examples, without intending to restrict the scope of the present invention.

EXAMPLE 1

Manufacturing of Non-Coated Plates

Pellets of copolymer material comprising about 80 mol-% of L-lactide and about 20 mol-% of glycolide were supplied by PURAC biochem by, Gorinchem, Holland. The pellets were formed such that they had an inherent viscosity of about 5.9 dl/g and a molecular weight Mv of about 336,000. The inherent viscosity was measured at 25° C. using 100 mg polymer per 100 ml of chloroform.

The pellets were extruded into a form of a cylindrical bar with a diameter of 6.0 mm using a single screw extruder (Axon BX-15, Axon Plastmaskiner, Sweden) and allowed to cool to ambient room temperature (20° C.). The extruded bar had an inherent viscosity of about 3.4 dl/g and a molecular weight Mv of about 158,000. The crystallinity of the extruded bar was about 1.5% and the glass transition temperature Tg was about 53° C. (as measured with differential scanning calorimeter, Perkin-Elmer DSC-7). To induce crystallinity the extruded bar was then annealed for 16 hours under vacuum (0.02 mbar) at 110° C. After annealing, the inherent viscosity of the bar was unchanged (about 3.4 dl/g) and the crystallinity was about 19%. The annealed bar was oriented uniaxially by drawing it through a heated tapered die (T=90° C.) to produce an oriented rod was a diameter of 3.0 mm (draw ratio of 4). After orientation the crystallinity of the material was over 20%.

The uniaxially oriented rod was oriented biaxially by compressing it between parallel stainless steel molding plates. A steel band of the thickness of 1.2 mm was placed between the molding plates on both sides of the rod (these bands determined the thickness of the plate after molding). The rod was preheated three minutes at 60° C. under low compression force (~0.1 kN), which prevented shrinking while allowing the material to become rubbery. After preheating the temperature of the compression molding plates was elevated stepwise at 10° C. increments (during 3 minutes) to 90° C. while elevating also compression force stepwise at 10 kN increments to 30 kN. The mold was then cooled rapidly (in 2 minutes) to room temperature (20° C.) with cooling water led into cooling channels in the walls of the mold. The mold was opened and the plate-like biaxially oriented preform was removed from the mold.

Figure 2B:
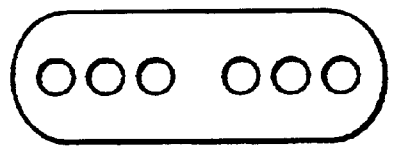
Figure 2C:
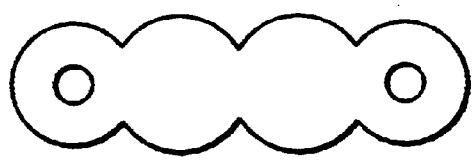
Figure 2D:
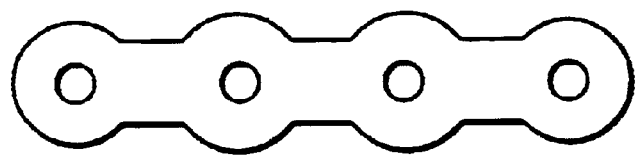

Such preforms were then processed further with drilling and grinding, producing plates having a configuration similar to the plate shown in FIG. 2B. The dimensions of machined plates were 1.2×5.5×40 mm. The holes had a diameter of 1.5 mm and they were located at 3 mm distance from each others. The plates were then gamma sterilized with a minimum dose of 2.5 MRad (25 kGy). After gamma irradiation the inherent viscosity of the plates was about 1.3 dl/g and the molecular weight Mv was about 42 000. The crystallinity of the plates was determined to be more than 20%. The flexural strength of 180 MPa was measured for the plates.

Figure 8A:
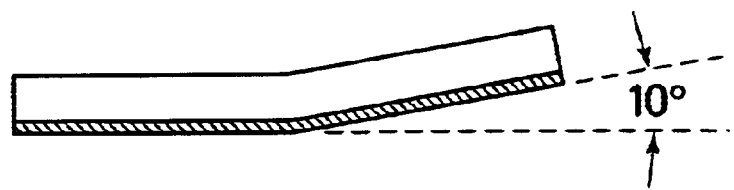
FIGS. 8A–8C show schematically the bending of plates of the invention at room temperature or at an elevated temperature.
Figure 8B:
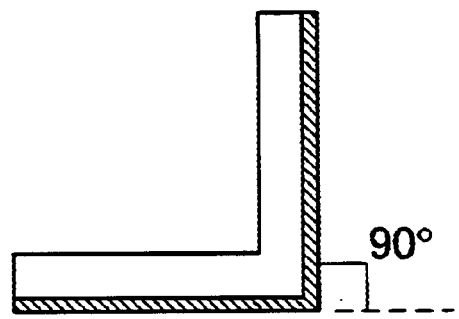
Figure 8C:
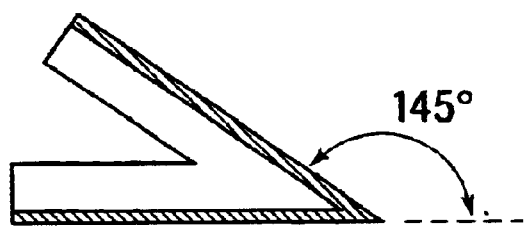

When the plates were bended at room temperature (20° C.) to angles of 10°, 90° and 145° out of the plane of the plates (see FIGS. 8A, B and C, respectively) they showed ductile plastic deformation and retained the desired bending angle just after the stress was relieved. It was shown that bending did not change the strength of the plates.

EXAMPLE 2

Manufacturing of Plates (Preforms) for Coating with an Osteoconductive Layer

Cylindrical rod with a diameter of 6.1±10.2 mm was made of P(L/DL)LA (70/30) with inherent viscosity 5.5 dl/g (trademark Resomer® LR708 of Boehringer Ingelheim, Ingelheim am Rhein, Germany), by single screw extrusion (with the same extruder as in Example 1). Rods were cooled to the ambient temperature (20° C.).

Extruded rods were oriented (and self-reinforced) by a die drawing method with the draw ratio of 4. Diameter of the drawn rods was 3.0±0.1 mm. Suitable drawing temperatures for used material were between 70–100° C.

About 150 mm long piece of the oriented, self-reinforced rod was set between two parallel compression moulding plates. The rod was preheated three minutes at 60±5° C. between the plates under gentle compression (<1 kN). After preheating the temperature of the compression moulding plates was elevated to 90° C. At the same time compression force was elevated to 30 kN. The plate that was thereby formed (thickness 1.2 mm) was cooled during 2 minutes to the temperature of 30° C. under a compression force of 30 kN and released from the mold. Total cycle time was 8 minutes. Such plates were machined mechanically to the final dimensions of 1.2 mm×3 mm×40 mm.

Coating with Thermal Compression

The oriented plates were coated with bioactive glass 13–93 spheres (glass manufacturer Abmin Technologies Ltd., Turku, Finland) which were spread over plate and implanted onto the plate by pressing between metallic plates covered with PTFE film.

Bioactive glass 13–93 spheres were produced by flame spraying. Glass composition was: 6 wt-% $Na_2O$, 12 wt-% $K_2O$, 5 wt-% $M_gO$, 20 wt-% CaO, 4 wt-% $P_2O_5$, 53 wt-% $SiO_2$ (Maria Brink, PhD Thesis, Åbo Akademi University, Finland 1997). Particle size distribution was 125–250 µm.

The coating was performed in the following way:

The plate and glass spheres were preheated ca. 1 min to 60–65° C. under pressure of <2 MPa. As soon as the temperature reached 60±5° C. pressure was increased to 4–10 MPa. The plates were kept under this pressure 1–2 min and during that time the temperature was increased up to 70° C. (max 80° C.). The plates were cooled to the temperature of 35° C. under pressure of 4–10 MPa and released to room conditions. The total cycle time was 3–4 min.

Some coated plates of the invention were placed in a phosphate buffer solution at 0.13 M, pH 7.4 and 37° C. to determine in vitro the change in strength over time as the plates degrade. After six weeks, the plates were shown to retain more than 70% of their original flexural strength, while the flexural strength was approximately zero at about 18 weeks.

Coating with a Solution Etching Method

One side of the oriented plate preform was etched at room temperature with Purasolv EL (Purac biochem bv, Gorinchem, The Netherlands) for 2 to 5 minutes. A monolayer of bioactive glass 13–93 spheres (same type glass spheres as above) were spread onto the bottom of a stainless steel plain mold and the plate preform was laid on top of the spheres so that the etched side was in contact with the glass spheres. The mold was closed with a flat cover on which a gentle compression of 2 MPa was applied at room temperature (23° C.) for 5 to 10 minutes. The total cycle was 7–15 min. The coated plates were kept under a vacuum for 12 hours to evaporate the solvent.

Both thermal compression and solution etching methods produced plates that were coated on one surface with a monolayer of bioactive glass spheres.

EXAMPLE 3

Hydrolysis of Bioactive Glass 13–93 Coated P(L/DL)LA Plates

Figure 9:
FIG. 9 shows a SR-P(L/DL)LA plate preform coated with bioactive glass spheres with a glass particle size distribution of 125–250 $\mu$m (scale bar=100 $\mu$m)

FIG. 9 shows a SEM micrograph of the glass coated self-reinforced P(L/DL)LA plate manufactured according to EXAMPLE 2 with the thermal compression method. Glass sphere size distribution was 125–250 µm (see FIG. 9).

Short term hydrolysis behavior, with hydroxy apatite deposition on the bioactive glass coated plates was studied in a simulated body fluid (SBF) (pH 7.4±0.2) at 37±1° C. Ratio of the glass coated surface area to solution volume was approx.0.01 $mm^{-1}$ and the solution volume to sample volume was greater than 20. Immersion times were from 6 hours to 7 days. After immersion, the specimens were rinsed with ultrapure water and ethanol, dried in a vacuum at 25° C. for 3 days and studied by scanning electron microscopy (SEM). Samples were coated with gold to SEM examination (JEOL T100, Japan).

Figure 10A:
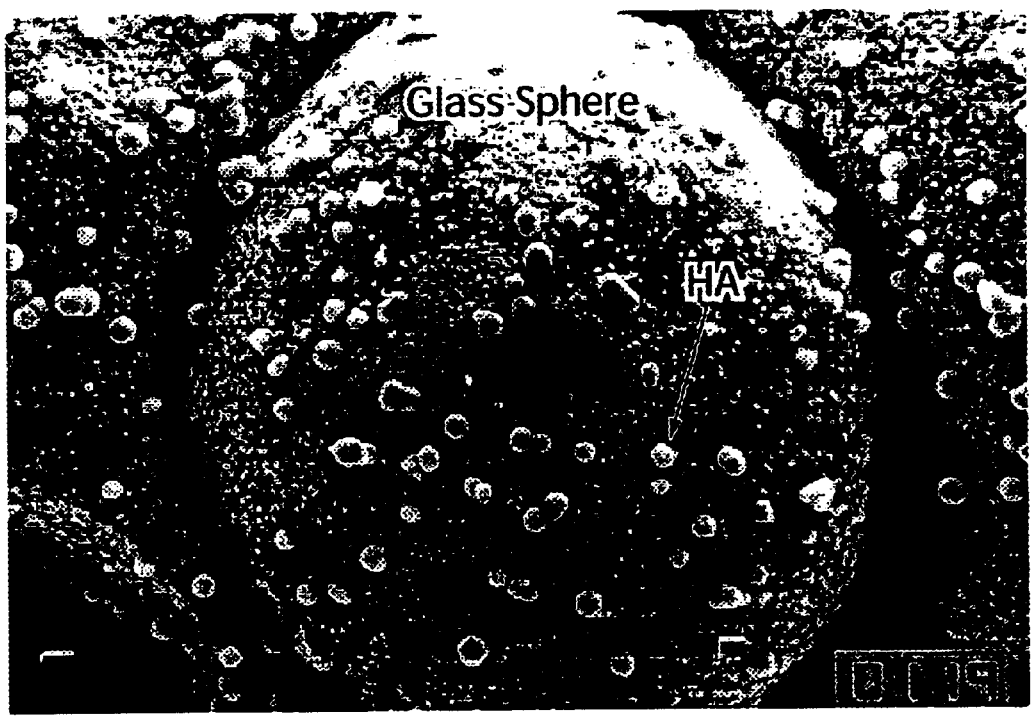
FIGS. 10A–10B show apatite precipitations, both at the glass sphere surface (A) and at the polymer substrate (B) (see arrows in the figures) after 72 hours immersion of coated plate in simulated body fluid (SBF) (scale bars in figs. 100 $\mu$m).
Figure 10B:
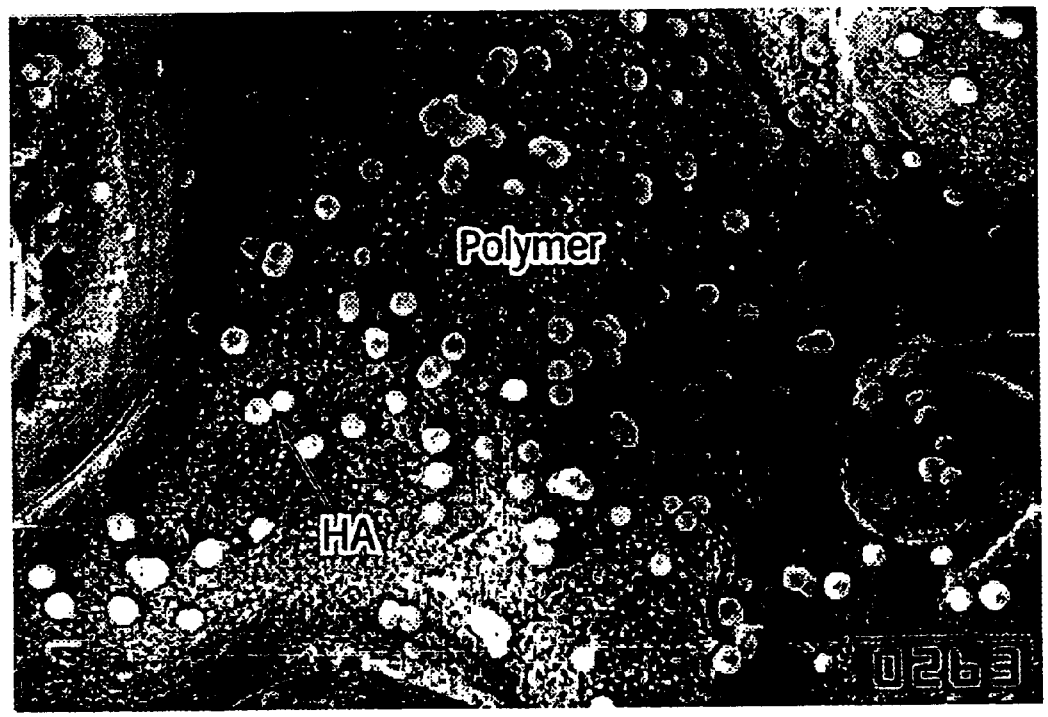
Figure 11:
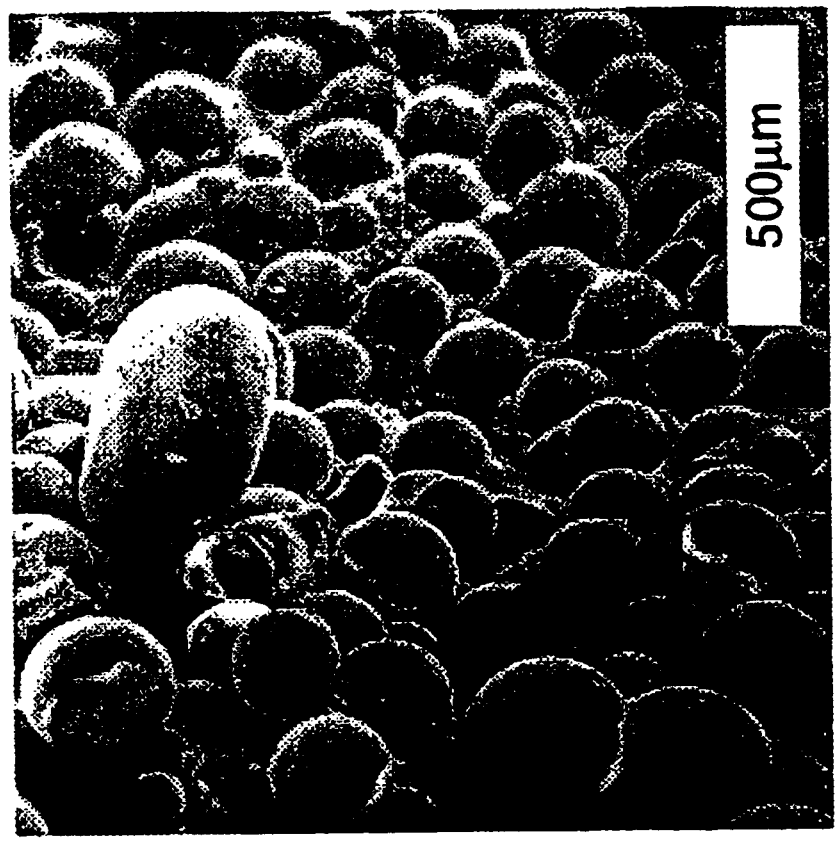
FIG. 11 is a SEM micrograph of the coated plate after bending deformation at room temperature.
Figure 11:
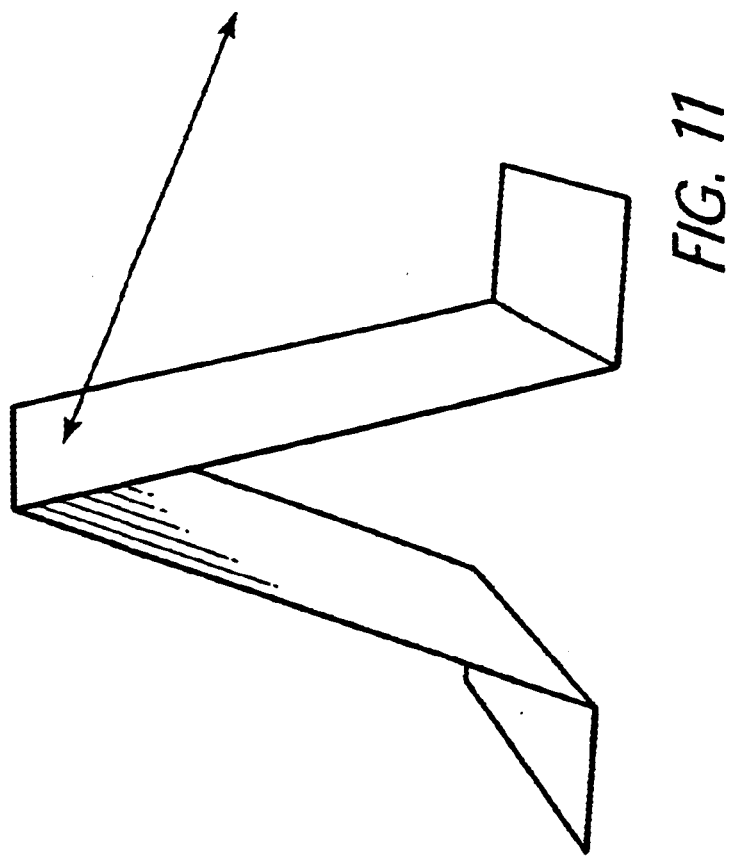

Immediate contact of the glass with the hydrolysis buffer was achieved due to the exposed glass sphere surfaces. This allowed bioactive glass surface reactions to start as soon as the contact to the hydrolysis buffer was established. Short term in vitro studies showed that the hydroxy apatite precipitation was formed within first 72 hours. FIG. 10 shows SEM micrographs of the glass coated self-reinforced P(L/DL)LA plate after 3 days hydrolysis. An apatite layer can be observed in FIG. 10A. In addition, apatite precipitation and a uniform apatite layer was formed onto the polymer matrix adjacent to the glass spheres (FIG. 10B). Precipitation was identified as an apatite (HA) by means of EDAX (EDAX, Philips XL 30) with Zaffaz program, Ca/P ratio being around 1.67 (stoichiometric value of HA).

Plate preforms were processed further with drilling and grinding producing plates having a configuration similar to the plate shown in FIG. 2B. The dimensions of machined plates were 1.2×5.5×40 mm. The holes had a diameter of 1.5 mm and they were located at 3 mm distance from each others. The plates were then gamma sterilized with a minimum dose of 2.5 MRad (25 kGy). After gamma irradiation the flexural strength of ca. 120 MPa was measured for the plates.

Because of exposed bioactive glass sphere surfaces, composite materials of the invention exhibit apatite precipitations rapidly without the need for mechanical processing, like grinding or cutting, of the material to expose the glass phase. Moreover, by using a glass sphere coating with exposed glass sphere surfaces, one can achieve a more rapid and uniform formation of an apatite layer onto the polymer matrix surface when compared to, for example, extruded, glass containing P(L/DL)LA composites, where the glass spheres are under a thin polymer layer. In the case of such extruded, glass containing, prior art composites, the thin polymer layer (skin) coating of glass spheres, was observed. Only after 7 days hydrolysis glass particles were observed to have started to resorb and apatite layer was formed onto the glass surface and only after 5 weeks some apatite precipitation was observed in adjacent polymer matrix near to the glass spheres.

After 6 weeks hydrolysis, the plates of the present invention retained over 70% of their original flexural strength, showing that they are suitable for bone fracture fixation purposes.

EXAMPLE 4

Bending of Coated Plates

When the plates of EXAMPLE 2 were bended at room temperature (23° C.) to angles of 10°, 90° and 145° C. out of the plane of the plates (see FIGS. 8A, B and C, respectively) they showed ductile plastic deformation and retained the desired bending angle just after the stress was relieved. It was shown that bending did not change the strength of the plates and that the coating was peeled off only at the bended area, but not elsewhere.

EXAMPLE 5

Manufacturing an Osteoconductive Bioabsorbable Plate from a PLLA Plate and Collagen Membrane by Glueing the Components with Racemic PLDLA Poly-L-lactic acid (PLLA) (Purac Biochem b.v.Gorinchem, The Netherlands) medical grade, highly purified polymer with weight average molecular weight ($M_w$) 233,000 Da was extruded to plate form using an Axon Bx15 extruder (screw ø 15 mm, L/D 24/1) and a flat plate die.The extruder temperatures were 210° C.–250° C. from the hopper to the die. The thickness of the plate was 0.3 mm.

A commercial collagen membrane Lyodura (manufactured by B.Braun Melsungen, AG, Germany) was chosen to be glued to the PLLA plates. The membrane had a non-woven structure and thickness of <1 mm.

Racemic poly-L,D-lactic acid (Boehringer Inegelheim, Ingelheim am Rhein, Germany) medical grade, highly purified polymer with intrinsic viscosity of 1.5 g/dl was used to glue the plate and collagen membrane together. PLDLA was dissolved into acetone (1 g/20 ml). In order to produce a completely dissolved mixture, the PLDLA and acetone mixture was left covered to the magnetic stirrer for 12 hours.

In glueing, the PLLA plates were thinly spread (painted) with the PLDLA—acetone solution described above. The collagen membrane was then gently overlaid on the wet, painted plates. The acetone was allowed to evaporate for 2 hours and the coated plates were then covered with a dust cover in a fume cupboard. Then the plates were kept for 12 hours in a vacuum oven at room temperature in order to remove the acetone residuals. The manufactured composite plates had a smooth PLLA surface on one side and a porous fibrous collagen surface on the other side.

What is claimed is:

1. A bioabsorbable osteosynthesis plate comprising at least one surface coated with osteopromoting fibers or fiber fabric.

2. The plate according to claim 1, wherein said osteopromoting coating is formed of bioactive glass.

3. The plate according to claim 1, wherein said osteopromoting coating is formed of collagen-based material.

4. The plate according to claim 1, wherein said osteopromoting coating is formed of demineralized bone.

5. The plate according to claim 1, wherein said osteopromoting coating comprises bioactive additives.

6. The plate according to claim 1, wherein said plate further comprises a plurality of preformed openings for receiving fasteners.

7. The plate according to claim 1, wherein said plate is capable of being deformed at room temperature.

8. The plate according to claim 1, wherein said plate comprises a mixture of (1) a material selected from the group of: bioabsorbable polymers, copolymers and polymer alloys, and (2) a material selected from the group of: bioactive glass particles and fibers.

9. A bone stabilization device for stabilizing a plurality of bone portions comprising: an osteopromoting bioabsorbable osteosynthesis plate comprising a material that is substantially deformable at room temperature, said plate having a plurality of fastener openings disposed therethrough, and said plate further comprising at least one surface that is coated with an osteopromoting coating comprising fibers or fiber fabric, whereby said plate is capable of stabilizing said plurality of bone portions for a period of at least four weeks in vivo.

10. The bone stabilization device according to claim 9, wherein said material from which said plate is formed comprises a mixture of (1) a material selected from the group of: bioabsorbable polymers, copolymers and polymer alloys, and (2) a material selected from the group of: bioactive glass particles and fibers.

11. The bone stabilization device according to claim 9 further comprising a plurality of surgical fasteners to secure said plate to said plurality of bone portions.

12. The bone stabilization device according to claim 11 wherein at least one of said fastener openings comprises a recessed portion for receiving one of said surgical fasteners.

13. The bone stabilization device according to claim 12 wherein at least one of said surgical fasteners includes a substantially conical portion for engaging at least a portion of one of said fastener openings.

14. A method for securing a plurality of bone portions using a bioabsorbable osteosynthesis plate, said method comprising the steps of:
providing a bioabsorbable osteosynthesis plate, said plate comprising at least one surface coated with osteopromoting fibers or fiber fabric;

deforming said osteosynthesis plate at room temperature;

securing said osteosynthesis plate to said plurality of bone portions so that said osteopromoting coating contacts said bone portions.

15. The method according to claim 14 further comprising the additional step of forming at least one opening through said plate for receiving a fastener.

16. The method according to claim 14, wherein said plate is deformed at room temperature a plurality of times.

17. The method according to claim 14, wherein said step of deforming said biocompatible osteosynthesis plate comprises the steps of:

(a) changing the shape of said biocompatible osteosynthesis plate while at room temperature;

(b) repeating step (a) until a desired configuration of said plate has been obtained.

18. The method according to claim 14, wherein said plate is deformable in each of its three perpendicular axes.

19. A bone stabilization device for stabilizing a plurality of bone portions, said bone stabilization device comprising: a resorbable osteosynthesis plate comprising a material which is selected from the following group: polylactide and polyglycolide homo- and copolymers, polyorthorsters, pseudo- polyaminoacids, and polyanhydrides, said plate having an osteopromoting coating on at least one surface of said plate comprising fibers or fiber fabric, whereby said plate is capable of stabilizing said plurality of bone portions for a period of at least for weeks in vivo.

20. The plate according to claim 19, wherein said material of said plate is oriented.

* * * * *

UNITED STATES PATENT AND TRADEMARK OFFICE
CERTIFICATE OF CORRECTION

PATENT NO.      : 6,692,498 B1
DATED           : February 17, 2004
INVENTOR(S)     : Niiranen et al.

It is certified that error appears in the above-identified patent and that said Letters Patent is hereby corrected as shown below:

Column 20,
Line 12, change "for" to -- four --.

Signed and Sealed this

Twelfth Day of October, 2004

JON W. DUDAS
*Director of the United States Patent and Trademark Office*